United States Patent [19]

Nose

[11] 4,013,564
[45] Mar. 22, 1977

[54] MULTIPURPOSE METABOLIC ASSIST SYSTEM

[75] Inventor: Yukihiko Nose, Cleveland Heights, Ohio

[73] Assignee: Takeda Chemical Industries, Ltd., Osaka, Japan

[22] Filed: Mar. 17, 1975

[21] Appl. No.: 559,395

[52] U.S. Cl. .............................. 210/434; 210/321 R
[51] Int. Cl.$^2$ ......................................... B01D 31/00
[58] Field of Search ...... 210/22, 321, 434, DIG. 23

[56] References Cited

UNITED STATES PATENTS

| 3,373,876 | 3/1968 | Stewart | 210/434 X |
| 3,449,245 | 6/1969 | Johnson et al. | 210/321 X |
| 3,579,441 | 5/1971 | Brown | 210/434 X |
| 3,608,729 | 9/1971 | Haselden | 210/321 |
| 3,727,612 | 4/1973 | Sayers et al. | 210/321 X |
| 3,742,946 | 7/1973 | Grossman | 210/321 X |
| 3,865,726 | 2/1975 | Chibata et al. | 210/321 K X |
| 3,888,250 | 6/1975 | Hill | 210/DIG. 23 X |

*Primary Examiner*—Frank A. Spear, Jr.
*Attorney, Agent, or Firm*—Wenderoth, Lind & Ponack

[57] ABSTRACT

A multipurpose metabolic assist system has an inlet passageway, an outlet passageway, a treated blood component passageway spaced from the inlet passageway and extending to the outlet passageway. The system has at least one space between at least a portion of the inlet passageway and a portion of the treated blood component passageway, and a particulate treatment agent for treating a component of the blood is packed in said space. At least a portion of the inlet passageway and the treated blood collection passageway which face the space are constituted by a porous membrane having pores of a size smaller than the size of the particles of the treatment agent and of a size for passing a component of the blood to be treated, and blocking passage of the remainder of the blood. A flow obstructor for producing an increased pressure is provided in the inlet passageway. When blood is supplied to the inlet passageway, the component of the blood to be treated is passed through the membranes and the treatment agent and the component is treated and the treated component is collected in the treated blood component passageway and supplied to the outlet passageway.

14 Claims, 11 Drawing Figures

MULTIPURPOSE METABOLIC ASSIST SYSTEM

BACKGROUND OF THE INVENTION

PRIOR ART

This invention relates to an apparatus for removing from the blood various wastes, toxic substances, and so on, without application of any mechanical force, such as centrifugation, sedimentation, etc., and without fear of hemolysis. In the apparatus, a portion of the plasma is separated by dialysis and filtration, is cleaned by absorption, degradation, chemical reactions, etc., and returned to the blood stream.

In the last 30 years, hemodialysis has been established as a good method of treating uremic patients. During these three decades, hemodialysis membranes comprised of a cellulose material have been used. In order to improve performance, various semipermeable membranes were developed and fabricated for use in hemodialysis (Proceedings, Annual Contractors' Conference 3–7, 1970–1974, NIH). Some of these membranes having a pore size less than $0.1\mu$ have also been used in so-called ultra filtration systems in which only molecules less than the size of the protein molecules were passed, the retained material with the protein therein being returned directly to the patient, and the material passed by the filter either being discarded or regenerated by chemical adsorbent and then returned to the patient.

A recent breakthrough has been the introduction of hemoperfusion techniques utilizing chemical adsorbents as a means of treating the uremic patient (Yatzidis, H., Nephron, 1:310, 1964). Various chemical adsorbents have since been used and some of the systems have been utilized for the actual treatment of the patients. However, one of the major problems which is always inherent in the use of chemical adsorbents is how to avoid small particles of the chemicals being mixed into the blood stream, since these systems require using direct perfusion of blood over the sorbents.

Techniques of microencapsulation of adsorbents were introduced to avoid this problem and also enhance blood compatibility of adsorbents (Chang, T.M., Science, 146:526). The incorporation of the chemical adsorbents, such as activated charcoal, into membrane materials or incorporating the adsorbents into fibers (Davis, T.A., et al., Proceedings, Annual Contractors' Conference, NIAMD, 7:111, 1974) were also attempted for the same reason.

Activated carbon and resins were also utilized for the treatment of acute hepatic insufficiency. The dramatic effect of this was demonstrated clinically utilizing hemoperfusion over activated carbon microencapsulated with hydrogel materials (Gazzard, B.G., et al., The Lancet, P. 1870, June 29, 1974).

However, whatever the technique utilized at this time, still the carryover of microparticles is one of the major problems associated with this type of system. For these systems, a filter is used. However, the most practical filter at this time which is utilized for extracorporeal circulation is an open mesh of 18 microns or larger. Any particles less than this size will go through the filters. If chemical adsorbents are used repeatedly, certainly many particles will be introduced into the vascular system and remain in the body. This is very hazardous, and it is a very difficult problem to solve, even with microencapsulation or improved packaging techniques (Andrade, J.E., et al., Proceedings, Annular Contractors' Conference, NIAMD, 7:113, 1974).

OBJECTS AND BRIEF SUMMARY OF THE INVENTION

It is therefore an object of the present invention to provide an apparatus which overcomes the disadvantages of the above-described methods and apparatus, and which is a simple yet effective means for removing undesirable substances from the blood.

These objects are achieved by an apparatus in which the undesirable substances are efficiently removed from the blood, and the blood cleaned by such processes as adsorption, decomposition, chemical and biological (enzymatic or bacteriological) reactions and returned to the body to prevent efflux of necessary substances. At the same time, the apparatus of this invention is so designed that even minute fragments of the treating material, covering material, etc. cannot enter the blood stream.

In the apparatus of this invention, the separate functions of fractionating the elements in the blood with a membrane and cleaning the plasma by adsorption, decomposition, chemical and biological reactions, etc. are combined so that the undesirable components and toxic substances can be safely removed from the blood while the minute particles that could cause an embolus are prevented from entering the blood stream.

The apparatus described in this patent application can avoid all the problems of escaping particles and overcome some inherent deficiencies of the present hemoperfusion systems. Since this concept can be adapted for various types of chemical adsorbents and biological treating materials, such as liver tissue preparations, enzyme systems, and microorganisms, this system can be used for a wide variety of purposes. With the apparatus of the invention, the proper chemical adsorbent or biological material for a specific clinical application can be used. Thus, the system can be called a "Multipurpose Metabolizer" or "Multipurpose Metabolic Assist System".

The concept of this approach is that, rather than requiring microencapsulation or membrane coating of the particles of treating material in an attempt to avoid direct contact with the blood, there is utilized a permeable membrane package for passing plasma therethrough. The membranes of the package can be hydrophilic or hydrophobic and permeable to the noncellular component of the blood, but not permeable to cellular components, and therefore should have a pore size of 0.05 to 1 micron in diameter. The treating material, whether it is sorbents, enzymes, cells, tissue, or microorganisms, is packaged into this membrane system and directly contacted by the non-cellular blood components. With this pore size, any particles which may get into the blood stream will be less than 1 micron, which is a range proven to be acceptable, even in a rather large quantity circulating in the body (Nose, Y. et al., Federation Proceedings, 29:1789, 1970).

Embodiments of the apparatus of the invention have a structure such that as the blood flows through the device over the membrane, the plasma can freely flow through the membrane and be processed and then be reunited with the mainstream of the blood. Thus, the effect of the chemical adsorbent or the enzyme, tissue, cell or microorganism can be achieved in the membrane package, but without the release of any particles which might otherwise obstruct the capillaries and cause permanent damage to the body. Since it is not required that the actual particles of treating material be encapsulated or membrane coated, which coating reduces their efficiency, the fabrication of this system is rather simple, easy, and reproducible, while the efficiency of the system is kept at a maximum. To avoid the consequences of membrane rupture and dangerous complications in the patient, a standard extracorporeal filter is recommended to be included in the blood return line. If a rupture of the membrane does take place, the mass of particles of the treating material will be released at once, and will immediately occlude the filter. Blood flow through the hemoperfusion system will stop at this point. Because of this, introduction of the microparticles to the patient can be prevented with minimum danger. The membrane to be selected should be strong enough to insure against accidental ruptures.

The concept of this approach is also very different from the ultra-filtration approach in that only the cellular components are retained by the membranes of the membrane package, thus allowing the plasma to pass, and in that all of the plasma is passed over the treatment material, not just a part thereof which has passed an ultra filtration membrane, as in the ultra filtration system.

BRIEF DESCRIPTION OF THE DRAWINGS

The invention will now be described in connection with the accompanying drawings, in which.

DETAILED DESCRIPTION OF THE INVENTION

Figure 1:
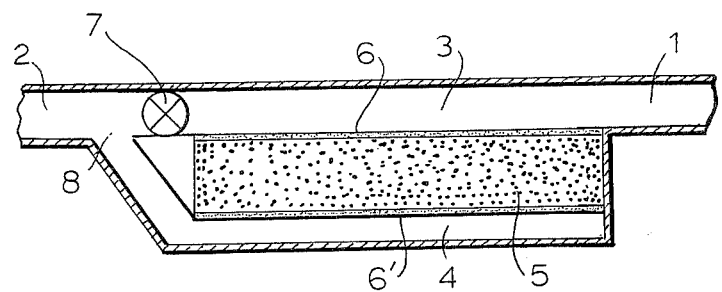
FIG. 1 is a diagrammatic view of a fundamental form of the apparatus of this invention showing the principle underlying the apparatus.

Referring first to FIG. 1, the apparatus has an inlet 1 through which the blood from the patient's blood vessel enters the apparatus, and an outlet 2 through which the cleaned blood returns to the blood vessel. An input passageway means 3 extends between inlet 1 and outlet 2 and has a differential pressure control throttle 7 at the downstream end thereof. A collection passageway means 4 for the plasma is provided at a point spaced from the input passageway means 3. A particulate treating agent 5, which is used for carrying out the adsorption, decomposition, chemical and biological reactions, etc., is provided in the space between passageway means 3 and 4. Porous membranes 6 and 6' are provided which have pores of a size which do not pass the cellular elements in the blood, such as the red and white cells, the platelets, etc. or particles of the treating agent 5, but which do pass the plasma, the undesirable substances contained in the plasma, and, in certain cases, additional substances gradually supplied from the treating agent, the pores having a size which ranges from 0.1 to 1$\mu$. Membrane 6 is provided in an opening from the passageway means 3 into the space occupied by the treatment agent 5 and membrane 6' is provided in an opening between this space and the collection passageway means 4. The differential pressure control throttle 7 generates a pressure difference across the membranes 6 and 6', and agent 5 for passing the fluid from the passageway means 3 through the membranes 6 and 6' and the treating agent 5, thereby cleaning the plasma and delivering it to the passageway means 4. This pressure may, in certain instances, be the spontaneous pressure caused by the flow of the blood itself in a particular configuration or length of the input passageway means 3, in which case the throttle 7 can be omitted. The input passageway means 3 and the collection passageway means 4 meet at a point of convergence 8, where the plasma depleted blood coming from the input passageway means 3 meets the cleaned plasma coming from the collection passageway means 4 to return together to the blood vessel. If necessary, the two streams can be returned independently to the blood vessel and, in that event, the converging arrangement of the passageway means can be omitted.

Figure 2:
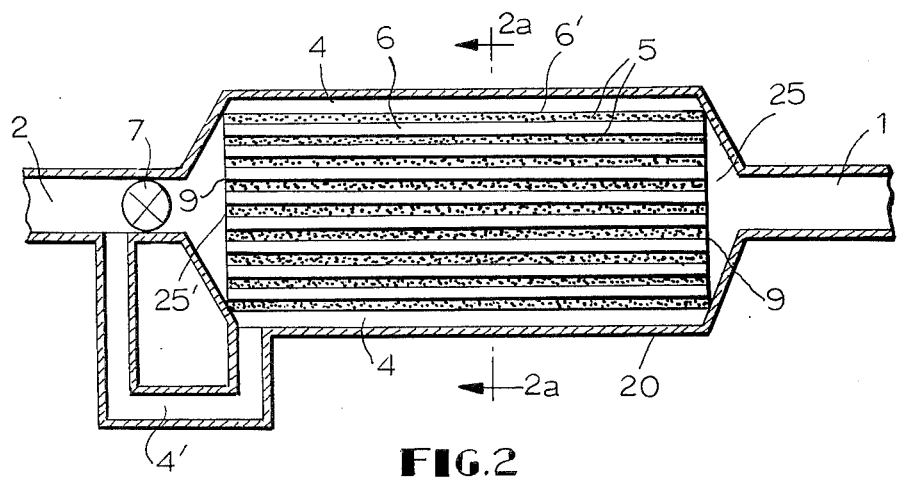
FIG. 2 is a longitudinal section of a first practical embodiment of the apparatus and FIG. 2a is a transverse section thereof taken along line 2a—2a of FIG. 2.
Figure 2A:
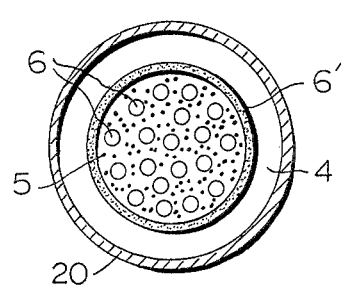

In the embodiment of FIGS. 2 and 2a, in which parts corresponding to the parts of the apparatus of 1 have numerals the same as in FIG. 1, the blood input passageway means 3 is in the form of a plurality of capillary tubes which are bundled at both ends, i.e. by a potting arrangement 9. Of course, the wall defining each capillary tube is the membrane 6, as shown clearly in FIG. 2a, which is a sectional view taken on line A–A' of FIG. 2.

The plurality of tubes forming the input passageway means 3 is furtheer surrounded by a membrane 6'. The space defined by and between membranes 6 and 6' is packed with a predetermined amount of an adsorbent or treating agent 5. The zone defined between an outer cylindrical wall 20 and the membrane 6 is the plasma collection passageway means 4. A distribution chamber 25 is provided within casing 20 between the inlet tube 1 and the one ends of the capillary tubes, and a collecting chamber 25' is provided between the other ends of the capillary tubes and the outer tube 2.

Thus, the patient's blood that must be treated enters the apparatus through inlet 1 and flows into the distribution chamber 25 from which it is distributed into the blood passageway means 3 constituted by the capillary tubes. In the capillary tubes, plasma is separated from the blood through the walls of the capillary tubes constituting the porous membrane 6 by the pressure of the flow thereof or under an externally applied pressure. The plasma depleted blood, of course, flows into the collecting chamber 25' and to the outlet 2. On the other hand, the plasma separated by membrane 6 is corrected by an adsorbent or treating material within the plasma treating chamber 5, passes through the membrane 6 and flows into the plasma collection passageway means 4. The plasma further flows through a plasma passageway 4' to converge with the plasma depleted blood at convergence point 8 and the combined flow is returned to the patient's body through the outlet 2. It should be noted that, in the above process, it is not essential at all that all the blood be fractionated into formed elements and plasma. The process can be effective when only a portion of the plasma is separated and treated. Any deficiency may be compensated for by increasing the number of times the blood is circulated through the apparatus, for example by a structure as shown in FIG. 2b.

Figure 2B:
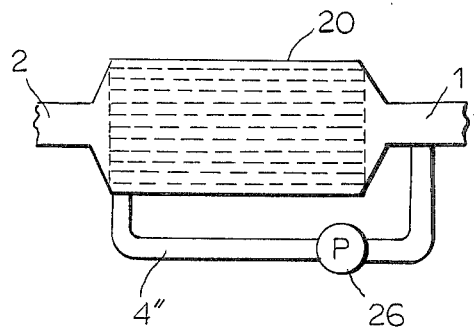
FIG. 2b is a view similar to FIG. 2 of a modified embodiment which recirculates the treated plasma.

FIG. 2b shows a structure similar to that of FIG. 2a, except that passageway 4'' instead of being connected downstream of outlet 2 is connected upstream of inlet 1 and has a pump 26 therein.

Figure 3:
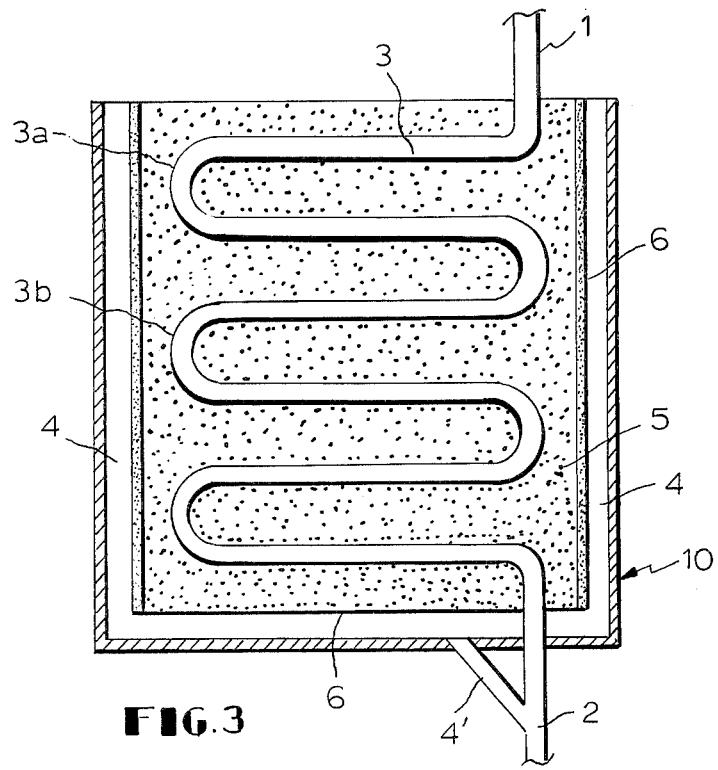
FIGS. 3 and 4 are longitudinal sections of modifications of another practical embodiment thereof.
Figure 4:
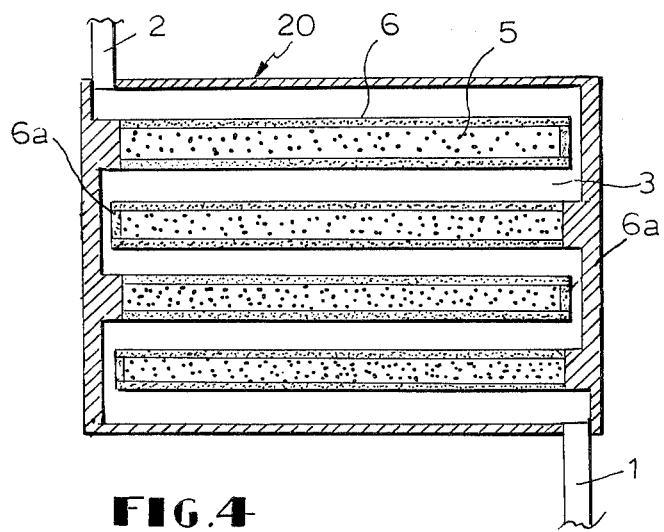
Figure 5:
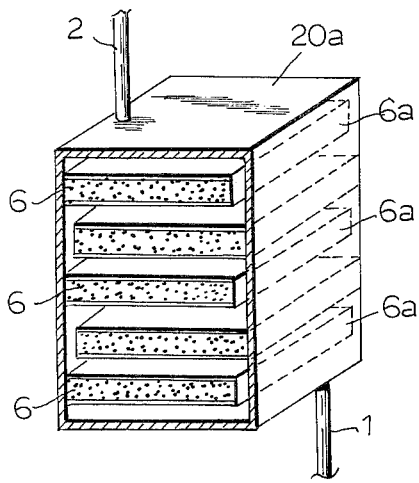
FIG. 5 is a partially cut away perspective view of the embodiment of FIG. 4.

FIG. 3 shows another embodiment. In this embodiment, the blood inlet passageway means 3 is formed in the form of a porous membrane 6, shaped as an envelope having folds 3a, 3b . . . , the portions of which are spaced from each other at predetermined intervals. The space around the folds 3a, 3b . . . is filled with the treating agent 5 contained in porous membrane 6' spaced inwardly from the wall of casing 10 to define the plasma collection passageway means 4. The blood entering from the inlet 1 is fractionated by having the plasma separated through the membrane 6 to leave a component including cellular elements. The plasma thus separated is corrected to the normal condition by the treating agent 5 and filtered into the plasma collection passageway means 4. The plasma then flows through plasma passageway 4' and converges with the plasma depleted blood to be returned to the patient's body through the outlet 2. In this embodiment, throttles have been omitted, since the folds of the envelope provided sufficient flow resistance to provide the necessary differential pressure. FIGS. 4 and 5 show still another embodiment of the apparatus of this invention. The feature which differentiates this embodiment from the apparatus of FIG. 3 is that the plasma which has been separated is treated in the plasma treating agent 5, and then passes back through the membrane 6 and returns to the blood again so that a portion of the blood is separated and treated.

Within a housing 20, of plastic or some other material inert to blood, is provided a plurality of horizontal porous membranes 6. These can be membranes sold as millipore filters by Millipore Corp. of Bedford, Mass., or they can be hydrophilic ester membranes, such as polyester sheets in which are reenforcing fabric and having a pore size of 1 micron, such as can be obtained from Zuricher Beuteltuchfabric et al. of Zurich, Switzerland. The lowermost membrane is spaced above the bottom of the housing 20 to define a blood inlet passageway means 3 therewith, and successive pairs of membranes 6 similarly spaced from each other are provided at intervals above the lowermost membranes. At the top of the housing is an uppermost membrane 6 spaced from the top of the housing to form a similar blood passageway means. The lowermost membrane is in fluid tight engagement with the one side wall of the housing 20, and there is a space between the other end thereof and the other side wall of the housing. The next higher pair of membrances has the end of the lower membrane thereof against the one side wall of the housing and the end of the upper membrane against the other side wall of the housing. This arrangement is repeated in the successive pairs of membranes and the uppermost membrane. The free ends of adjacent membranes are connected by vertically extending membrane portions 6a. The remaining edges of the membranes are in tight engagement with the inner walls of the housing, so that there is formed a sinuous passageway from the inlet 1 in the bottom of the housing to the outlet 2 at the top of the housing, the passageway having one dimension equal to the spacing between the membranes and the bottom and top of the housing and between the membranes of a pair of membranes, and the other dimension equal to the depth of the housing from the front to the back, as viewed in FIGS. 4 and 5. The spaces between the pairs of membranes and the lowermost and uppermost membranes is packed with treatment agent 5. Outlet 2 extends out of the end of the uppermost portion of the sinuous passageway. If necessary to control the pressure within the pasageway, the dimension across the passageway at the turns can be reduced, for example to about 50% of the dimension of the horizontal portions. As a pracitical matter, however, by causing the blood to run vertically upwardly through the apparatus, and by properly dimensioning the apparatus, the necessary pressure differentials can be produced within the apparatus.

In operation, blood to be treated is fed into the apparatus through the inlet 1, and when the sinuous passageway defined by the membranes 6 and 6a is filled, the pressure in lower part of the passageway will be sufficiently high, due to the resistance of the flow of blood therethrough to produce the necessary differential across the membranes 6 and 6a to cause the plasma to separate and flow into the space occupied by the treatment agent 5, while the plasma depleted blood will continue to flow through the passageway. In the upper portion of the apparatus, the pressure differential will be reversed, that is, the pressure within the passageway will be less than the pressure of the plasma being treated by the treatment agent, and plasma which has been treated will flow through the membranes back into the stream of plasma depleted blood, and the combined materials will flow out the outlet 2.

In one actual embodiment of the apparatus of FIGS. 4 and 5, the porous membranes were "millipore" filters as described above having a pore diameter of $0.22\mu$, and each treatment space was 7 cm long, 7 cm wide, and 1 cm high, and having a volume of 49 cm$^3$. Each such space was filled with steam-activated coconut shell activated carbon having a particle size distribution of $125-250\mu$, made by Takeda Chemical Industries, Ltd. The housing 20 was of polypropylene. There were five plasma treating spaces. The porous membranes in the adjacent pairs were spaced at intervals of 2 millimeters so as to produce a passageway having a cross-sectional area 2 mm × 1 cm.

This embodiment contained a total of about 100 grams of activated carbon, and the total surface area of the porous membranes to which the blood had access was 525 cm$^2$. The volume of blood necessary to prime this apparatus was approximately 62 cubic centimeters. With this apparatus, the blood of a patient with renal insufficiency was satisfactorily treated in a period of about 3 to 6 hours.

It will, of course, be appreciated that the embodiment of FIGS. 4 and 5 can be oriented with the plates positioned vertically and the inlet and outlet extending horizontally. This arrangement is shown in FIG. 6.

Figure 6:
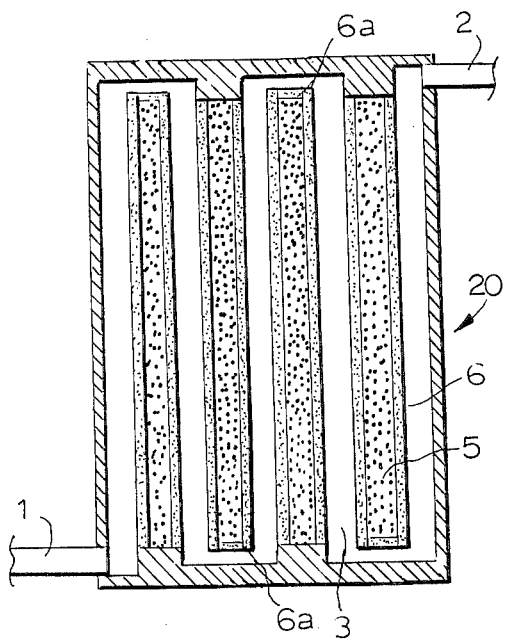
FIG. 6 is a view similar to FIG. 4 of a modification of the embodiment of FIG. 4 in which the plates are oriented vertically, rather than horizontally.

In order to avoid the formation of stagnant spots in the flow passages of the devices of FIGS. 4–6, screen material 27 can be placed in the passages. This screen should be substantially the same in area as the area of the plate-shaped membranes, so that they cover substantially the whole length and width of the passages 3. This will insure substantially even flow of the liquid material through the passages, the flow being evenly distributed by the strands of material forming the screen. The material of the screen 27 should be one which is inert to the liquid material being passed through the device, e.g. the same material as that of the polypropylene housing.

Figure 8:
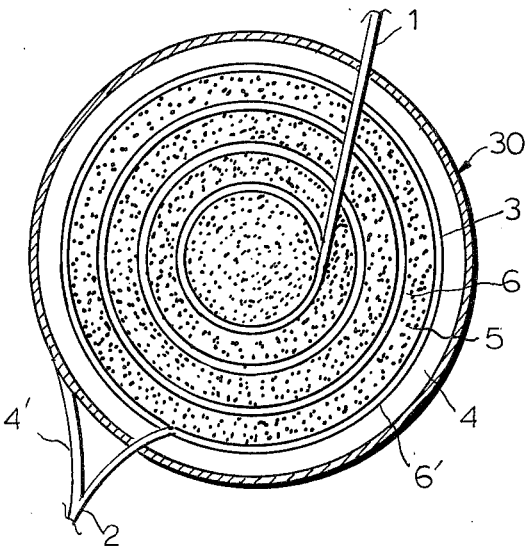
FIG. 8 is a transverse section of still another practical embodiment thereof.

The embodiment of FIG. 8 is similar in concept to that of FIG. 2, but is shaped somewhat differently. Within a cylindrical housing 30 is a membrane 6' spaced inwardly from the wall of the housing to define an annular plasma collection passageway means 4 with a branch flow tube 4' extending therefrom to the outlet tube 2. The space within the membrane 6' has a spirally coiled membrane 6, preferably in the form of an envelope which defines the inlet passageway means 3, and into which the inlet 1 extends. The space within the membrane 6' and surrounding the envelope is filled with treatment material 5. The axial dimension of the housing 30 and the envelope can be relatively long, as compared to the diameter of the housing, thereby increasing the capacity of the apparatus and the area of membrane 6 exposed to the treatment material.

The membranes can be commercially available membranes with pore diameters of the pores in the membrane designated as about 0.05 to $2\mu$, and preferably about 0.1 to $1\mu$. Reference to the pore sizes means that the membranes have pores, most of which are about the size designated, but they can have a few pores larger and smaller than the sizes designated.

The pore size is selected mainly according to the type of treating agent. Thus, higher efficiencies are obtained with membranes having a larger pore size, e.g. near $1\mu$, for treating agents of comparatively large particles size, such as activated carbon, alumina, ion exchange resin, etc., while for treating agents, the particles of which are soft or tend to swell at the molecular level (macromolecules with giant skeletal structures), such as oxidized starch and insolubilized enzymes having sephalose skeletons, or for biological treating materials, membranes with pores of a smaller diameter, e.g. 0.1 to $0.2\mu$ are preferably employed for safety reasons, i.e. to prevent leakage of the treating agent. Furthermore, when it is necessary to control the release time, as it is in the case with a drug for instillation, the membrane must also be controlled with reference to such factors as the properties of the drug, whether it is in the form of microcapsules, etc.

In the present invention, while the required surface area of the porous membrane varies with the patient to be dealt with, the type of treating agent, the pore size of the membrane, etc., it is in some cases sufficient to provide an area smaller than that required in the case of dialytic apparatus incorporating a semi-permeable membrane. This means that the volume of extracorporeal blood being circulated is much smaller than in a dialytic apparatus, and the apparatus of the invention is thus much safer.

Figure 9:
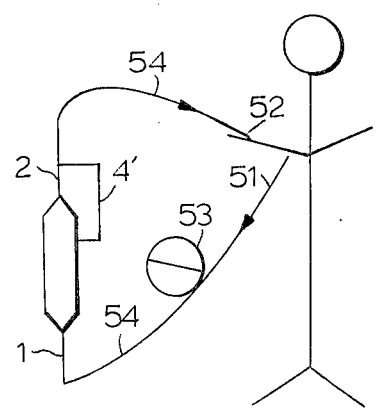
FIG. 9 is a diagrammatic view of how the apparatus can be connected to a patient.
Figure 7:
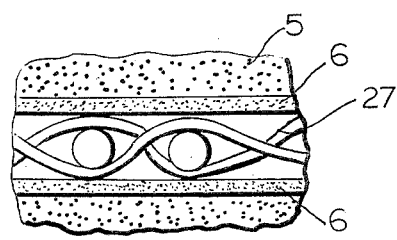
FIG. 7 is a detail of a modified form of the apparatus shown in FIG. 4.

FIG. 9 shows the apparatus of FIG. 2 as used with a patient. Designated by reference numeral 51 is the patient's artery, and by 52 is his vein, to which the blood inlet and outlet, respectively, of the apparatus are connected by blood tubes 54. Indicated by numeral 53 is a by blood tubes 54. Indicated by numeral 53 is a pump, commonly an occlusive pump, adapted to pump the blood. This, however, is not necessarily indispenssable and, in some cases, may be omitted where the patient's own blood pressure is sufficient.

In addition to the above arrangement, an infrared lamp, an electric heater, lukewarm water or the like, though not shown, may be used for keeping the apparatus warm. Thus, the patient's blood flows from the artery to the blood tubing 54 and, under the influence of the pressure generated by said blood pump 53, further into the apparatus of this invention where the plasma is treated and returned to the vein through tubing 54.

Although the treatment agent is normally only for removal of substances from the plasma, it can also act either along or in combination with an adsorbent or the like, to add desired substances to the blood. A soluble material can, for example, be mixed in with the treatment agent.

The following is a partial list of the treating agents which can be employed in the apparatus of this invention.

| TREATING AGENT | AMOUNT ORDINARILY USED | PURPOSE |
| --- | --- | --- |
| 1. Adsorbent | | |
| Activated carbon | 50–500g | Removal of drug erroneously taken. Removal of metabolic wastes in renal insufficiency, hepatitis and other cases. |
| Adsorbent resins | 50–500g | Removal of metabolic wastes in renal insufficiency, hepatitis and other cases. |
| Alumina | 50–500g | Removal of phosphate ions in renal insufficiency, etc. |
| Zirconium oxide | 50–500g | Removal of phosphate ions in renal insufficiency, etc. |
| Zirconium phosphate | 50–500g | Removal of ammonia in hepatic coma and other maladies. |
| 2. Reactive Polymers | | |
| Oxidized Starch (Cellulose Oxide) | 50–500g | Removal of ammonia in combined use with urease treatment in hepatic coma and renal insufficiency, or with asparaginase treatment in leukemia. |
| Ion exchange resins | 1–20g | Removal of K in renal insufficiency. |
| 3. Insolubilized Enzymes | | |
| Urease | Depends on enzymatic activity | Removal of urea in renal insufficiency (in combination with an agent for removal of ammonia). |
| Asparaginase | Depends on enzymatic activity | Removal of asparaginase in leukemia, and removal of urea in renal insufficiency (in combination with an agent for removal of ammonia). |
| Tissue preparation, e.g. liver | 800g (wet weight) | Supplies liver function in general, particularly for synthesis. |
| Urine dependant bacteria | Depends on bacterial metabolic activity | Removal of urea and nitrogen compounds. |
| 4. Drugs for Instillation | | |

-continued

| TREATING AGENT | AMOUNT ORDINARILY USED | PURPOSE |
| --- | --- | --- |
| Nutrients | Therapeutic or prophylactic dose | The release time is controlled by microencapsulation, molecular weight increase, etc. |
| Hormones | Therapeutic of prophylactic dose | The release time is controlled by microencapsulation, molecular weight increase, etc. |

The apparatus of this invention has a number of features. First, by the mere procedure of connecting the blood inlet 1 and outlet 2 to the blood vessel, the plasma in the blood is separated by the membrane, cleaned by the treating agent, and returned to the blood vessel so that the desired cleaning effect can be carried out expediently and with efficiency. When it is desired to increase the influx velocity of blood, a blood pump having simple construction can be provided on the inlet side of the apparatus. A second feature of the present apparatus is that of safety. Thus, because the flows of blood and of cleaned plasma are kept separate from the treating agent by a compact membrane, particles of the treating agent that could otherwise cause embolus on influx into the blood stream are completely prevented from entering the blood stream. The particle fraction of not more than $.2\mu$ means that the membrane does not permit passage thereacross of blood platelets which are smallest of all the elements formed in the blood, nor does it pass the smallest bacteria. A third feature is that there is a broad latitude possible in the selection of the treating agent, because the treating agent does not pass through the membrane irrespective of particle size, rigidity, shape, quality of the coating, the presence or absence of a coating, whether it is solid or fluid, and other factors. A fourth feature is the feasibility of using several types of treating agent in a mixture or isolated from each other so that the undesired substances, toxic substances, etc. with different properties and behaviors can be simultaneously adsorbed. This feature imparts unusual versatility to the apparatus of this invention. A fifth feature is that because the membrane and the treating agent can be selected quite independently, it is now possible to have a suitable combination of the membrane and the treating agent. Thus, it is possible to employ treating agents such as oxidized starch, insoluble enzymes, etc. which are difficult to coat, as well as treating agents such as activated carbon, alumina, etc., which do not lend themselves well to forming into a membranous structure. It is also not necessary that in the production of a membrane the possible influences of processing conditions upon the treating agent be taken into consideration. A sixth feature of the apparatus of this invention is that because the treated plasma is returned in its entirety to the blood vessel, there is substantially no loss of essential substances. A seventh feature of the present apparatus is that because the cycle of the plasma passing through the membrane where it is cleaned by the treating agent, passing again through the membrane and then converging with the blood is repeated without a loss of the blood, plasma and essential substances, it is possible to increase the efficiency of treatment by varying the form and arrangement of the apparatus as exemplified by the embodiments illustrated in FIGS. 2 − 8.

An eighth feature is that it is easy to make a compact system, because the membrane has a lot of large pores so plasma can be effectively exposed freely to the uncoated reactors in the package.

A ninth feature is that the system can be kept sterile and is easy to store and transport, because it is packaged dry and all of the treating materials are secured in the membrane package.

A tenth feature is that the system requires no complicated rinsing procedure prior to its use.

What is claimed is:

1. An apparatus for treating blood, comprising an inlet passageway means, an outlet passageway means, a treated blood component passageway means spaced from said inlet passageway means and being connected directly to said outlet passageway means, said apparatus having at least one space between at least a portion of said inlet passageway means and a portion of said treated blood component passageway, a particulate treatment agent for treating a component of the blood for removing undesirable materials from the blood, said agent being taken from the group consisting of an adsorption agent, a decomposition agent, an agent reacting chemically for removal of the undesirable materials and an agent reacting biologically for removal of the undesirable materials, said treatment agent being packed in said space, at least a portion of the inlet passageway means and the treated blood component passageway means which face said space being constituted by a porous membrane having pores of a size smaller than the size of the particles of the treatment agent and of the size for passing a component of the blood to be treated, and blocking passage of the remainder of the blood, and flow obstruction means for producing an increased pressure in said inlet passageway means, whereby when blood is supplied to the inlet passageway means, only the component of the blood to be treated is passed through the membrane of the inlet passageway means and said treatment agent, and the component is treated and the treated component from which the undesirable material has been removed is passed through the membrane of the blood component passageway and is collected in the treated blood component passageway means and supplied to said outlet passageway means and rejoins the remainder of the blood therein.

2. An apparatus as claimed in claim 1 in which said membranes have pores of a size ranging from 0.05 to $20\mu$ whereby the plasma component of blood can be passed and the cellular components will not be passed by the membranes.

3. An apparatus as claimed in claim 2 in which the treatment agent is a biological treatment agent and the pores have a size ranging from 0.1 to $0.2\mu$.

4. An apparatus as claimed in claim 2 in which the treatment agent is a material taken from the group consisting of activated carbon, alumina and ion exchange resin, and the pores have a size of about $1\mu$.

5. An apparatus as claimed in claim 1 further comprising a housing, a membrane within said housing and enclosing a space therewithin, said membrane being spaced from the inside of said housing to define a treated blood component space, the space within said membrane having said treatment material therein, and porous membrane conduit means extending into said space and constituting said inlet passageway means.

6. An apparatus as claimed in claim 1 further comprising a housing, said housing having the treatment material therein, and membrane means positioned within said housing for defining the inlet passageway means, outlet passageway means and treated blood component passageway means therein.

7. An apparatus for treating blood, comprising a housing, said housing having an inlet at one end thereof and an outlet at the other end thereof, an annular membrane within said housing defining a space therewithin and spaced from the inside wall of said housing to define a treated blood component passageway therebetween, a plurality of tubular membranes extending through said annular membrane parallel with the axis thereof and spaced from each other and from said annular membrane, the space within said annular membrane around said tubular membranes having a particulate treatment agent for treating a component of the blood packed therein for removing undesirable materials from the blood, said agent being taken from the group consisting of an adsorption agent, a decomposition agent, an agent reacting chemically for removal of the undesirable materials and an agent reacting biologically for removal of the undesirable materials, said membranes being porous membranes having pores of a size smaller than the size of the particles of the treatment agent and of a size for passing the component of the blood to be treated and blocking passage of the remainder of the blood, a treated blood component return conduit connected between said treated blood component passageway and said outlet, and flow obstruction means in the outlet between said housing and the point at which said conduit is connected thereto, whereby when blood is supplied to the housing inlet, only the component of the blood to be treated is passed through the tubular membranes and said treatment agent, and the component is treated and the treated component from which the undesirable material has been removed is passed through the annular membrane and is collected in the treated blood component passageway and supplied to said housing outlet and rejoins the remainder of the blood therein.

8. An apparatus for treating blood, comprising a housing, said housing having an inlet at one end thereof and an outlet at the other end thereof, an annular membrane within said housing defining a space therewithin and spaced from the inside wall of said housing to define a treated blood component passageway therebetween, a plurality of tubular membranes extending through said annular membrane parallel with the axis thereof and spaced from each other and from said annular membrane, the space within said annular membrane around said tubular membranes having a particulate treatment agent for treating a component of the blood packed therein for removing undesirable materials from the blood, said agent being taken from the group consisting of an adsorption agent, a decomposition agent, an agent reacting chemically for removal of the undesirable materials and an agent reacting biologically for removal of the undesirable materials, said membranes being porous membranes having pores of a size smaller than the size of the particles of the treatment agent and of a size for passing the component of the blood to be treated and blocking passage of the remainder of the blood, a treated blood component return conduit connected between said treated blood component passageway and said inlet, and pump means in said return conduit, whereby when blood is supplied to the housing inlet, only the component of the blood to be treated is passed through the tubular membranes and said treatment agent, and the component is treated and the treated component from which the undesirable material has been removed is passed through the annular membrane and is collected in the treated blood component passageway and recycled to the inlet by said pump means.

9. An apparatus for treating blood, comprising a housing, an annular membrane within said housing defining a space therewithin and spaced from the inside wall of said housing to define a treated blood component passageway therebetween, a flattened tubular membrane coiled within said annular membrane around an axis parallel with the axis of said annular membrane and with the spires of the coil spaced from each other and from said annular membrane, the space within said annular membrane around said spires having a particulate treatment agent for treating a component of the blood packed therein for removing undesirable materials from the blood, said agent being taken from the group consisting of an adsorption agent, a decomposition agent, an agent reacting chemically for removal of the undesirable materials and an agent reacting biologically for removal of the undesirable materials, said membranes being porous membranes having pores of a size smaller than the size of the particles of the treatment agent and of a size for passing the component of the blood to be treated and blocking passage of the remainder of the blood, a blood inlet tube connected to one end of said coiled tubular membrane, a blood outlet tube connected to the other end of said coiled tubular membrane, and a treated blood component return conduit connected between said treated blood component passageway and said outlet tube, whereby when blood is supplied to the interior of the tubular membrane, only the component of the blood to be treated is passed through the tubular membrane and said treatment agent, and the component is treated and the treated component from which the undesirable material has been removed is passed through the annular membrane and is collected in the treated blood component passageway and supplied to said blood outlet tube and rejoins the remainder of the blood therein.

10. An apparatus for treating blood, comprising a housing, a membrane within said housing defining a space therewithin and spaced from the inside wall of said housing to define a treated blood component passageway therebetween, a blood inlet tube extending into said housing and said space, a tubular membrane connected to the end of said blood inlet tube and extending in a sinuous path through said space, and blood outlet tube connected to the other end of said tubular membrane and extending out of said space and said housing, the space within said membrane and around said tubular membrane having a particulate treatment agent for treating a component of the blood packed therein for removing undesirable materials from the blood, said agent being taken from the group consisting of an adsorption agent, a decomposition agent, an agent reacting chemically for removal of the undesirable materials and an agent reacting biologically for removal of the undesirable materials, said membranes being porous membranes having pores of a size smaller than the size of the particles of the treatment agent and of a size for passing the component of the blood to be treated and blocking passage of the remainder of the blood, and a treated blood component return conduit connected between said treated blood component passageway and said outlet tube, whereby when blood is supplied to the blood inlet tube, only the component of the blood to be treated is passed through the tubular membrane and said treatment agent, and the component is treated and the treated component from which the undesirable material has been removed is passed through the annular membrane and is collected in the treated blood component passageway and supplied to said blood outlet tube and rejoins the remainder of the blood therein.

11. An apparatus for treating blood, comprising a housing, a plurality of spaced parallel plate-shape membranes mounted in said housing, a portion of the periphery of each membrane being spaced from the interior wall of the housing and the remainder of the periphery being in fluid tight engagement with the interior wall of the housing, the membrane adjacent one wall of the housing being spaced from said one wall to define therewith a blood inlet passageway and the membrane adjacent a wall of the housing opposite the said one wall being spaced from said lastmentioned wall to define therewith a blood outlet passageway, the remaining membranes being in pairs and defining between them passageways, all of said passageways having a cross-sectional area in a direction parallel to the membranes equal to the cross-sectional area of said housing in said direction, the pairs of membranes being spaced from each other and the spaces between the pairs of membranes and said membrane adjacent said one wall of the housing and said membrane adjacent the opposite wall of the housing having a particulate treatment for treating a component of the blood packed therein for removing undesirable materials from the blood, said agent being taken from the group consisting of an adsorption agent, a decomposition agent, an agent reacting chemically for removal of the undesirable materials and an agent reacting biologically for removal of the undesirable materials, said membranes being porous membranes having pores of a size smaller than the size of the particles of the treatment agent and of a size for passing the component of blood to be treated and blocking passage of the remainder of the blood, and passageway wall means extending between the portions of the peripheries of the pairs of membranes which are spaced from the wall of the housing and extending along the walls of the housing and defining therewith transverse passageway portions, said transverse passageway portions being at one end of the membrane adjacent the one wall of the housing and the next adjacent pair of membranes, at the other end of said next adjacent pair of membranes and the still next adjacent pair of membranes, and at alternate ends of the succeeding pairs of membranes for defining a sinuous passageway through the housing, the dimension of the transverse passageway portions in the direction between the passageway wall means and the wall of the housing being less than the dimension between parallel membranes of the pairs of membranes for creating a constriction in the sinuous passageway, whereby when blood is supplied to the blood inlet passageway, only the component of the blood to be treated is passed through the upstream plate-shaped membranes of the pairs of membranes and said treatment agent, and the component is treated and the treated component from which the undesirable material has been removed is passed through the downstream membranes of the pairs of membranes and rejoins the blood in the sinuous passageway.

12. An apparatus as claimed in claim 11 in which said membranes are horizontally positioned in the housing.

13. An apparatus as claimed in claim 11 in which the membranes are vertically positioned in said housing.

14. An apparatus as claimed in claim 11 in which at least one of the spaces between a pair of parallel membranes has a screen therein having a size the same as the size of the membrane and being of a material inert to the blood for evening the flow through the passageway.

* * * * *